(12) United States Patent
Hasenberg et al.

(10) Patent No.: US 10,633,334 B2
(45) Date of Patent: Apr. 28, 2020

(54) SYNTHESIS OF ASYMMETRICAL SULFIDE COMPOUNDS AND ASYMMETRICAL ETHER COMPOUNDS

(71) Applicant: Chevron Phillips Chemical Company LP, The Woodlands, TX (US)

(72) Inventors: Daniel M. Hasenberg, Kingwood, TX (US); Kenneth M. Lassen, Bartlesville, OK (US); Jason L. Kreider, Copan, OK (US); Henry Hwu, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 16/291,018

(22) Filed: Mar. 4, 2019

(65) Prior Publication Data

US 2019/0270703 A1 Sep. 5, 2019

Related U.S. Application Data

(60) Provisional application No. 62/753,965, filed on Nov. 1, 2018, provisional application No. 62/638,348, filed on Mar. 5, 2018.

(51) Int. Cl.
| | |
|---|---|
| *C07C 319/20* | (2006.01) |
| *B01J 21/04* | (2006.01) |
| *B01J 23/882* | (2006.01) |
| *C07C 319/06* | (2006.01) |
| *C07C 43/03* | (2006.01) |
| *C07C 41/14* | (2006.01) |
| *C07C 321/14* | (2006.01) |

(52) U.S. Cl.
CPC ............. *C07C 319/20* (2013.01); *B01J 21/04* (2013.01); *B01J 23/882* (2013.01); *C07C 41/14* (2013.01); *C07C 43/03* (2013.01); *C07C 319/06* (2013.01); *C07C 321/14* (2013.01)

(58) Field of Classification Search
None
See application file for complete search history.

(56) References Cited

U.S. PATENT DOCUMENTS

| | | |
|---|---|---|
| 4,005,129 A | 1/1977 | Zehner |
| 4,059,636 A | 11/1977 | Kubicek |
| 4,277,623 A | 7/1981 | Kubicek |
| 4,510,336 A | 4/1985 | Hearn |
| 4,537,994 A | 8/1985 | Roberts |
| 5,712,357 A | 1/1998 | Basset et al. |
| 2007/0135658 A1 | 6/2007 | Hasenberg et al. |
| 2019/0270702 A1 | 9/2019 | Hasenberg et al. |

OTHER PUBLICATIONS

McAllan et al., J. Amer. Chem. Soc., 1951, 73:3627-3632. (Year: 1951).*
Ma et al., Current Organic Chem., 2007, 11:477-482. (Year: 2007).*
International Search Report and the Written Opinion of the International Searching Authority in PCT/US2019/020533 dated May 10, 2019, 15 pages.
International Search Report and the Written Opinion of the International Searching Authority in PCT/US2019/020540 dated May 10, 2019, 16 pages.
McAllan et al., "The Preparation and Properties of Sulfur Compounds Related to Petroleum. I. The Dialkyl Sulfides and Disulfides," Journal of the American Chemical Society 1951, vol. 73, No. 8, pp. 3627-3632.

* cited by examiner

*Primary Examiner* — Clinton A Brooks
*Assistant Examiner* — Kofi Adzamli
(74) *Attorney, Agent, or Firm* — Merchant & Gould P.C.

(57) ABSTRACT

The present invention discloses methods for synthesizing asymmetrical sulfide compounds and asymmetrical ether compounds from a variety of ether, sulfide, alcohol, and thiol reactants that are contacted in the presence of a suitable catalyst. Conversions of the limiting reactant to the desired asymmetrical sulfide or asymmetrical ether compound generally exceed 50%.

14 Claims, 11 Drawing Sheets

SYNTHESIS OF ASYMMETRICAL SULFIDE COMPOUNDS AND ASYMMETRICAL ETHER COMPOUNDS

REFERENCE TO RELATED APPLICATIONS

This application claims the benefit of U.S. Provisional Patent Application No. 62/638,348, filed on Mar. 5, 2018, and U.S. Provisional Application No. 62/753,965, filed on Nov. 1, 2018, the disclosures of which are incorporated herein by reference in their entirety.

FIELD OF THE INVENTION

The present disclosure relates to processes for producing asymmetrical sulfide compounds and asymmetrical ether compounds from a variety of ether, sulfide, alcohol, and thiol reactants that are contacted in the presence of a catalyst.

BACKGROUND OF THE INVENTION

Asymmetrical sulfide and ether compounds can be prepared by various synthesis techniques, but such techniques often require harsh or corrosive reaction conditions, or result in significant byproducts. Accordingly, the present invention is generally directed to synthesis schemes to produce the asymmetrical sulfide or asymmetrical ether compounds in high yield and with minimal reaction byproducts.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

In one aspect, a process for producing an ether compound having formula $R^1$—O—$R^2$ is disclosed, and in this aspect, the process can comprise contacting a first ether compound having formula $R^1$—O—$R^1$, a second ether compound having formula $R^2$—O—$R^2$, and a catalyst, to form a reaction mixture comprising the ether compound having formula $R^1$—O—$R^2$.

In another aspect, a process for producing a sulfide compound having formula $R^1$—S—$R^2$ and an ether compound having $R^1$—O—$R^2$ is disclosed, and in this aspect, the process can comprise contacting an ether compound having formula $R^2$—O—$R^2$, a sulfide compound having formula $R^1$—S—$R^1$, and a catalyst, to form a reaction mixture comprising the sulfide compound having formula $R^1$—S—$R^2$ and the ether compound having $R^1$—O—$R^2$.

In another aspect, a process for producing a sulfide compound having formula $R^1$—S—$R^2$ is disclosed, and in this aspect, the process can comprising contacting a sulfide compound having formula $R^1$—S—$R^1$, an alcohol compound having formula $R^2$—OH, and a catalyst, to form a reaction mixture comprising the sulfide compound having formula $R^1$—S—$R^2$.

In another aspect, a process for producing an ether compound having formula $R^1$—O—$R^2$ is disclosed, and in this aspect, the process can comprise contacting an ether compound having formula $R^1$—O—$R^1$, an alcohol compound having formula $R^2$—OH, and a catalyst, to form a reaction mixture comprising the ether compound having formula $R^1$—O—$R^2$.

In another aspect, a process for producing a sulfide compound having formula $R^1$—S—$R^2$ is disclosed, and in this aspect, the process can comprise contacting a sulfide compound having formula $R^1$—S—$R^1$, a thiol compound having formula $R^2$—SH, and a catalyst, to form a reaction mixture comprising the sulfide compound having formula $R^1$—S—$R^2$.

In yet another aspect, a process for producing a sulfide compound having formula $R^1$—S—$R^2$ is disclosed, and in this aspect, the process can comprise contacting an ether compound having formula $R^1$—O—$R^1$, a thiol compound having formula $R^2$—SH, and a catalyst, to form a reaction mixture comprising the sulfide compound having formula $R^1$—S—$R^2$.

In still another aspect, a process for producing a sulfide compound having formula $R^1$—S—$R^2$ is disclosed, and in this aspect, the process can comprise contacting a first sulfide compound having formula $R^1$—S—$R^1$, a second sulfide compound having formula $R^2$—S—$R^2$, and a catalyst, to form a reaction mixture comprising the sulfide compound having formula $R^1$—S—$R^2$.

Consistent with these and other aspects of the invention, $R^1$ and $R^2$ in these processes independently can be a $C_1$ to $C_{18}$ substituted or unsubstituted, cycloalkyl group or linear or branched alkyl group. Generally, $R^1$ and $R^2$ are different to produce the asymmetrical sulfide compounds and asymmetrical ether compounds encompassed herein.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description and examples.

DEFINITIONS

Figure 1:
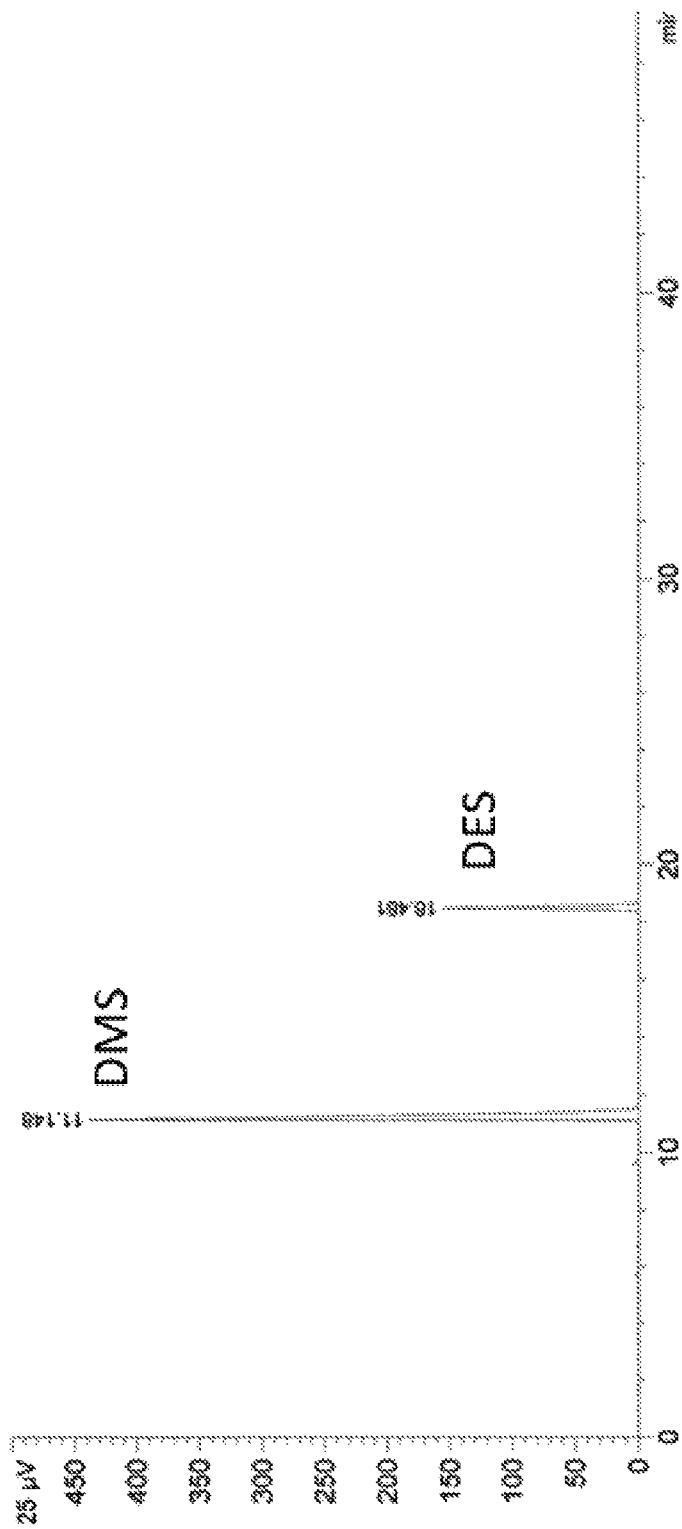
FIG. 1 presents a gas chromatograph plot of the blended feed of dimethyl sulfide and diethyl sulfide, which was used in Examples 1-15.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the compounds, compositions, processes, or methods described herein are contemplated with or without explicit description of the particular combination. Additionally, unless explicitly recited otherwise, any aspect or feature disclosed herein can be combined to describe inventive compounds, compositions, processes, or methods consistent with the present disclosure.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contact product," "contacting," and the like, are used herein to describe methods and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the methods and compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Consequently, depending upon the circumstances, a "contact product" can be a mixture, a reaction mixture, or a reaction product. Likewise, "contacting" two or more components can result in a reaction product or a reaction mixture.

In this disclosure, while compositions and processes are described in terms of "comprising" various components or steps, the compositions and processes also can "consist essentially of" or "consist of" the various components or steps, unless stated otherwise.

The terms "a," "an," and "the" are intended to include plural alternatives, e.g., at least one. For instance, the disclosure of "a catalyst" is meant to encompass one catalyst, or mixtures or combinations of more than one catalyst, unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ alkyl group, or in alternative language, an alkyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkyl group), and also including any combination of ranges between these two numbers (for example, a $C_2$ to $C_4$ and a $C_{12}$ to $C_{16}$ alkyl group).

Similarly, another representative example follows for the molar ratio of component (a) to component (b) consistent with aspects of this invention. By a disclosure that the molar ratio can be in a range from about 1:1.5 to about 1:10, the intent is to recite that the molar ratio can be any ratio in the range and, for example, can be equal to about 1:1.5, about 1:2, about 1:3, about 1:4, about 1:5, about 1:6, about 1:7, about 1:8, about 1:9, or about 1:10. Additionally, the molar ratio can be within any range from about 1:1.5 to about 1:10 (for example, from about 1:2 to about 1:6), and this also includes any combination of ranges between about 1:1.5 and about 1:10 (for example, the ratio can be in a range from about 1:1.5 to about 1:5, or from about 1:7 to about 1:9). Further, in all instances, where "about" a particular value is disclosed, then that value itself is disclosed. Thus, the disclosure of a molar ratio from about 1:1.5 to about 1:10 also discloses a molar ratio from 1:1.5 to 1:10 (for example, from 1:2 to 1:6), and this also includes any combination of ranges between 1:1.5 and 1:10 (for example, the ratio can be in a range from 1:1.5 to 1:5, or from 1:7 to 1:9). Likewise, all other ranges disclosed herein should be interpreted in a manner similar to these examples.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

All disclosed product yields are based on the limiting reactant in the respective reaction, unless explicitly stated otherwise. For example, the limiting reactant in a process for synthesizing an asymmetrical sulfide and/or ether compound can be component (a) and, therefore, the conversions and yields are based on the initial quantity of component (a).

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are processes for producing asymmetrical sulfide compounds using at least one symmetrical sulfide reactant, and processes for producing asymmetrical ether compounds using at least one symmetrical ether compound. The synthesis reactions can be conducted in a fixed bed reactor containing a solid catalyst.

Synthesizing Asymmetrical Sulfide and Ether Compounds

An ether or sulfide compound having the formula $R^1$—X—$R^2$ (III) can be produced in two general synthesis schemes. Consistent with some aspects of this invention, the process to produce the compound having formula (III) can comprise contacting (a) a first ether or sulfide compound having formula $R^1$—X—$R^1$ (F), (b) a second ether or sulfide compound having formula $R^2$—X—$R^2$ (G), and (c) a catalyst, to form a reaction mixture comprising the ether or sulfide compound having formula (III). Consistent with other aspects of this invention, the process to produce the compound having formula (III) can comprise contacting (a) an ether or sulfide compound having formula $R^1$—X—$R^1$ (F), (b) an alcohol or thiol compound having formula $R^2$—XH (H), and (c) a catalyst, to form a reaction mixture comprising the ether or sulfide compound having formula (III). Independently, each X in these formulas can be sulfur or oxygen. However, as would be recognized by those of skill in the art, the selection for X in each formula is not unlimited. For instance, if X is oxygen in formula (F) and formula (G), then X is oxygen in formula (III), e.g., an asymmetrical ether compound is produced. Likewise, if X is sulfur in formula (F) and formula (H), then X is sulfur in formula (III), e.g., an asymmetrical sulfide compound is produced.

From these two general synthesis schemes, several specific processes for producing ether and/or sulfide compounds are provided. A first process in accordance with this invention is directed to a process for producing an ether compound having formula (I):

$$R^1\text{—O—}R^2 \tag{I}$$

The first process can comprise contacting:
(a) a first ether compound having formula (A),

$$R^1\text{—O—}R^1 \tag{A}$$

(b) a second ether compound having formula (B),

$$R^2\text{—O—}R^2 \tag{B; and}$$

(c) a catalyst;

to form a reaction mixture comprising the ether compound having formula (I).

A second process in accordance with this invention is directed to a process for producing a sulfide compound having formula (II) and an ether compound having formula (I):

$$R^1\text{—S—}R^2 \tag{II}$$

$$R^1\text{—O—}R^2 \tag{I}$$

The second process can comprise contacting:
(a) an ether compound having formula (B),

$$R^2\text{—O—}R^2 \tag{B}$$

(b) a sulfide compound having formula (C),

$$R^1\text{—S—}R^1 \tag{C; and}$$

(c) a catalyst;

to form a reaction mixture comprising the sulfide compound having formula (II) and the ether compound having formula (I).

A third process in accordance with this invention is directed to a process for producing a sulfide compound having formula (II):

$$R^1\text{—S—}R^2 \tag{II}$$

The third process can comprise contacting:
(a) a sulfide compound having formula (C),

$$R^1\text{—S—}R^1 \tag{C}$$

(b) an alcohol compound having formula (D),

$$R^2\text{—OH} \tag{D; and}$$

(c) a catalyst;

to form a reaction mixture comprising the sulfide compound having formula (II).

A fourth process in accordance with this invention is directed to a process for producing an ether compound having formula (I):

$$R^1—O—R^2 \quad (I).$$

The fourth process can comprise contacting:
(a) an ether compound having formula (A), $$R^1—O—R^1 \quad (A);$$

(b) an alcohol compound having formula (D), $$R^2—OH \quad (D); \text{ and}$$

(c) a catalyst;
to form a reaction mixture comprising the ether compound having formula (I).

A fifth process in accordance with this invention is directed to a process for producing a sulfide compound having formula (II):

$$R^1—S—R^2 \quad (II).$$

The fifth process can comprise contacting:
(a) a sulfide compound having formula (C), $$R^1—S—R^1 \quad (C);$$

(b) a thiol compound having formula (E), $$R^2—SH \quad (E); \text{ and}$$

(c) a catalyst;
to form a reaction mixture comprising the sulfide compound having formula (II).

A sixth process in accordance with this invention is directed to a process for producing a sulfide compound having formula (II):

$$R^1—S—R^2 \quad (II).$$

The sixth process can comprise contacting:
(a) an ether compound having formula (A), $$R^1—O—R^1 \quad (A);$$

(b) a thiol compound having formula (E), $$R^2—SH \quad (E); \text{ and}$$

(c) a catalyst;
to form a reaction mixture comprising the sulfide compound having formula (II).

A seventh process in accordance with this invention is directed to a process for producing a sulfide compound having formula (II):

$$R^1—S—R^2 \quad (II).$$

The seventh process can comprise contacting:
(a) a first sulfide compound having formula (C), $$R^1—S—R^1 \quad (C);$$

(b) a second sulfide compound having formula (J), $$R^2—S—R^2 \quad (J); \text{ and}$$

(c) a catalyst;
to form a reaction mixture comprising the sulfide compound having formula (II).

Generally, the features of the first, second, third, fourth, fifth, sixth, and seventh processes for producing asymmetrical sulfide compounds and/or asymmetrical ether compounds (e.g., the particular reactants, the catalyst, and the conditions under which the asymmetrical sulfide and/or asymmetrical ether compound is/are formed, among others) are independently described herein and these features can be combined in any combination to further describe the disclosed first, second, third, fourth, fifth, sixth, and seventh processes to produce an asymmetrical sulfide compound and/or an asymmetrical ether compound. Moreover, additional process steps can be performed before, during, and/or after the contacting/reacting step of these processes, and can be utilized without limitation and in any combination to further describe the first, second, third, fourth, fifth, sixth, and seventh synthesis processes, unless stated otherwise.

Formulas (I), (II), (III), (A), (B), (C), (D), (E), (F), (G), (H), and (J) are not designed to show stereochemistry or isomeric positioning of the different moieties (e.g., these formulas are not intended to show cis or trans isomers), although such compounds are contemplated and encompassed by these formulas. In these formulas, $R^1$ can be a $C_1$ to $C_{18}$ substituted or unsubstituted, cycloalkyl group or linear or branched alkyl group, and $R^2$ can be a $C_1$ to $C_{18}$ substituted or unsubstituted, cycloalkyl group or linear or branched alkyl group. It is contemplated that $R^1$ and $R^2$ can be the same or different; however, to produce an asymmetrical sulfide or an asymmetrical ether, $R^1$ and $R^2$ are different.

$R^1$ in these formulas can be a $C_1$ to $C_{18}$ substituted or unsubstituted, cycloalkyl group or linear or branched alkyl group. In one aspect, for example, $R^1$ can be a $C_1$ to $C_{14}$ substituted or unsubstituted, cycloalkyl group or linear or branched alkyl group, while in another aspect, $R^1$ can be a $C_1$ to $C_{12}$ substituted or unsubstituted, cycloalkyl group or linear or branched alkyl group, and in yet another aspect, $R^1$ can be a $C_1$ to $C_8$ substituted or unsubstituted, cycloalkyl group or linear or branched alkyl group.

Consistent with aspects of the present invention, $R^1$ can be a cycloalkyl group; alternatively, $R^1$ can be a linear alkyl group; or alternatively, $R^1$ can be a branched alkyl group. Regardless of whether $R^1$ is a cyclic, linear, or branched alkyl group, $R^1$ can be unsubstituted, or can be substituted with any suitable substituent, any suitable number of substituents, and at any suitable position(s) that conforms to the rules of chemical valence.

$R^1$ can be a $C_1$ to $C_{18}$ linear or branched alkyl group in certain aspects of this invention. Thus, $R^1$ can be a $C_1$ to $C_{14}$ linear or branched alkyl group, a $C_1$ to $C_{12}$ linear or branched alkyl group, a $C_1$ to $C_8$ linear or branched alkyl group, or a $C_1$ to $C_6$ linear or branched alkyl group. Accordingly, in some aspects, $R^1$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a decyl group, or a dodecyl group.

In other aspects, the alkyl group which can be $R^1$ in these formulas can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group; alternatively, a methyl group, an ethyl group, or an iso-propyl group; alternatively, a methyl group or an ethyl group; alternatively, a methyl group; alternatively, an ethyl group; alternatively, a n-propyl group; alternatively, an iso-propyl group; alternatively, a n-butyl group; alternatively, an iso-butyl group; alternatively, a sec-butyl group; alternatively, a tert-butyl group; alternatively, a n-pentyl group; alternatively, an iso-pentyl group; alternatively, a sec-pentyl group; alternatively, a neopentyl group; alternatively, a tert-amyl group; alternatively, a n-hexyl group; alternatively, a n-heptyl group; alternatively, a n-octyl group; or alternatively, or a n-dodecyl group.

$R^1$ can be a cycloalkyl group in certain aspects of this invention. Thus, $R^1$ can be a $C_3$ to $C_{18}$ cycloalkyl group, a $C_4$ to $C_{12}$ cycloalkyl group, a $C_4$ to $C_{10}$ cycloalkyl group, or a $C_5$ to $C_8$ cycloalkyl group. Accordingly, in some aspects, $R^1$ in these formulas can be a cyclobutyl group, a cyclopentyl group, a cyclohexyl group, a cycloheptyl group, or a cyclooctyl group; alternatively, a cyclobutyl group; alternatively, a cyclopentyl group; alternatively, a cyclohexyl group; alternatively, a cycloheptyl group; or alternatively, a cyclooctyl group.

In accordance with another aspect of this invention, any alkyl group disclosed herein (cycloalkyl, linear alkyl, or branched alkyl) can be substituted with one or more substituents. Each non-hydrogen substituent(s) for the substituted alkyl group independently can be a $C_1$ to $C_{18}$ is hydrocarbyl group; alternatively, a $C_1$ to $C_5$ hydrocarbyl group; or alternatively, a $C_1$ to $C_6$ hydrocarbyl group. Thus, the hydrocarbyl substituent can be a benzyl group, a phenyl group, a tolyl group, or a xylyl group, and the like, and, therefore, $R^1$ in these formulas can be, for instance, a phenyl-substituted alkyl group. Additionally, the hydrocarbyl substituent can be a $C_1$ to $C_6$ linear or branched alkyl group and, therefore, $R^1$ in these formulas can be, for instance, an alkyl-substituted cycloalkyl group, such as a methylcyclohexyl group.

An illustrative non-hydrocarbon substituent that can be present on any alkyl group disclosed herein (cycloalkyl, linear alkyl, or branched alkyl) is a hydroxy group (—OH group). Thus, $R^1$ can be a methyl alcohol or methanol group (—CH$_2$OH), an ethyl alcohol or ethanol group (—CH$_2$CH$_2$OH), a propanol group, a butanol group, a pentanol group, a hexanol group, and so forth.

Referring now to $R^2$ in these formulas, $R^2$ can be any $C_1$ to $C_{18}$ substituted or unsubstituted, cycloalkyl group or linear or branched alkyl group disclosed herein for $R^1$ in these formulas. Thus, for example, $R^2$ can be any cycloalkyl group, linear alkyl group, or branched alkyl group disclosed herein, and further, $R^2$ can be unsubstituted, or can be substituted with any suitable substituent or any substituent disclosed herein, any suitable number of substituents, and at any suitable position(s) that conforms to the rules of chemical valence.

As noted herein, for the production of an asymmetrical sulfide and/or an asymmetrical ether, $R^1$ and $R^2$ are different. Therefore, in one aspect of this invention, $R^1$ can be a methyl group, and $R^2$ can be any $C_2$ to $C_{18}$ substituted or unsubstituted, cycloalkyl group or linear or branched alkyl group disclosed herein (e.g., $R^2$ can be an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group). In another aspect of this invention, $R^1$ can be an ethyl group, and $R^2$ can be any $C_3$ to $C_{18}$ substituted or unsubstituted, cycloalkyl group or linear or branched alkyl group disclosed herein (e.g., $R^2$ can be a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, n-octyl group, or a n-dodecyl group).

An illustrative and non-limiting example of the ether compound having formula (I) is methyl ethyl ether. Another illustrative and non-limiting example of the ether compound having formula (I) is methyl iso-propyl ether. Additional illustrative and non-limiting examples of the ether compound having formula (I) include methyl tert-butyl ether (CAS No. 1634-04-4), methyl tert-amyl ether, and the like.

An illustrative and non-limiting example of the sulfide compound having formula (II) is methyl ethyl sulfide (CAS No. 624-89-5). Another illustrative and non-limiting example of the sulfide compound having formula (II) is methyl isopropyl sulfide. Additional illustrative and non-limiting examples of the sulfide compound having formula (II) include methyl dodecyl sulfide, ethyl octyl sulfide, n-pentyl n-heptyl sulfide, and the like.

Generally, the appropriate procedure for the contacting (or reacting) step in the process for producing an asymmetrical sulfide and/or an asymmetrical ether is not particularly limited. For instance, the step of contacting (or reacting) component (a) (or compound (a)), component (b) (or compound (b)), and the catalyst (c) can comprise contacting component (a), component (b), and the catalyst (c) in any order that produces an acceptable yield of the desired sulfide and/or ether compound. Typically, component (a) and component (b) are combined first, following by contacting the mixture of (a) and (b) with the catalyst (c).

The processes to produce the asymmetrical sulfide and asymmetrical ether compounds can be conducted at any suitable temperature and for any suitable period of time. Representative and non-limiting ranges for the temperature of the contacting step (or for the formation of the asymmetrical sulfide and/or the asymmetrical ether) can include from about 200° C. to about 500° C., from about 250° C. to about 500° C., from about 200° C. to about 450° C., from about 250° C. to about 450° C., from about 125° C. to about 400° C., from about 200° C. to about 400° C., from about 200° C. to about 350° C., from about 250° C. to about 400° C., or from about 250° C. to about 350° C. These temperature ranges also are meant to encompass circumstances where the contacting step (or the formation of the asymmetrical sulfide and/or the asymmetrical ether) is performed at a series of different temperatures, instead of at a single fixed temperature, falling within the respective temperature ranges, wherein at least one temperature is within the recited ranges.

Similarly, the time period for contacting component (a), component (b), and catalyst (c), or for the formation of the asymmetrical sulfide and/or the asymmetrical ether, is not particularly limited, and can be conducted for any suitable period of time. In some aspects, the time period can be least about 1 min, at least about 5 min, at least about 10 min, at least about 30 min, at least about 1 hr, at least about 2 hr, at least about 5 hr, or at least about 10 hr. In other aspects, the time period can be from about 30 sec to about 48 hr, from about 1 min to about 24 hr, from about 5 min to about 8 hr, from about 30 min to about 8 hr, or from about 1 hr to about 6 hr.

Often, the process for forming the asymmetrical sulfide and/or the asymmetrical ether can be a flow process and/or a continuous process. In such circumstances, the limiting reactant-catalyst contact time (or reaction time) can be expressed in terms of weight hourly space velocity (WHSV)—the ratio of the weight of the limiting reactant which comes in contact with a given weight of catalyst per unit time (units of g/g/hr).

While not limited thereto, the WHSV employed for the process of producing an asymmetrical sulfide and/or an asymmetrical ether can have a minimum value of 0.01, 0.02, 0.05, 0.1, 0.25, or 0.5; or alternatively, a maximum value of 5, 4, 3, 2.5, 2, or 1. Generally, the WHSV can be in a range from any minimum WHSV disclosed herein to any maximum WHSV disclosed herein. In a non-limiting aspect, the WHSV can be in a range from about 0.01 to about 5; alternatively, from about 0.01 to about 3; alternatively, from about 0.01 to about 1; alternatively, from about 0.02 to about 4; alternatively, from about 0.02 to about 3; alternatively, from about 0.05 to about 2; alternatively, from about 0.05 to about 1; alternatively, from about 0.1 to 4; alternatively, from about 0.25 to about 3; alternatively, from about 0.25 to about 2; alternatively, from about 0.5 to about 4; alternatively, from about 0.5 to about 2; or alternatively, from about 0.5 to about 1. Other WHSV ranges are readily apparent from this disclosure. Any suitable reactor or vessel can be used to form the asymmetrical sulfide and/or the asymmetrical ether, non-limiting examples of which can include a flow reactor, a continuous reactor, a packed tube, and a stirred tank reactor, including more than one reactor in series or in parallel, and including any combination of reactor types and arrangements.

In one aspect, the process for producing the asymmetrical sulfide and/or the asymmetrical ether can comprise contacting component (a) and component (b) in the vapor phase with the catalyst (e.g., the solid catalyst). Additionally or alternatively, the process for producing the asymmetrical sulfide and/or the asymmetrical ether can comprise contacting component (a) and component (b) with a fixed bed of the catalyst.

While not being limited thereto, the contacting step and/or the formation of the asymmetrical sulfide and/or the asymmetrical ether can be conducted at a reaction pressure in a range from about 50 to about 850 psig (344 to 5860 kPag). Other representative and non-limiting ranges for the reaction pressure can include from about 50 to about 500 psig (344 to 3447 kPag), from about 100 to about 400 psig (689 to 2758 kPag), from about 150 to about 400 psig (1034 to 2758 kPag), from about 200 to about 450 psig (1379 to 3103 kPag), or from about 200 to about 350 psig (1379 to 2413 kPag).

The molar ratio of component (a) to component (b)—the molar ratio of (a):(b)—is not particularly limited, and generally can fall within a range from about 10:1 to about 1:10. Typical ranges for the molar ratio of (a):(b) can include, but are not limited to, from about 5:1 to about 1:5, from about 4:1 to about 1:4, from about 3:1 to about 1:3, from about 2:1 to about 1:2, or from about 1.5:1 to about 1:1.5.

Certain ratios of components during the contacting step can prove advantageous with respect to the yield and purity of the desired asymmetrical sulfide or the desired asymmetrical ether. In one aspect, the molar ratio of component (a) to component (b)—the molar ratio of (a):(b)—can be less than or equal to about 1:1, less than or equal to about 1:1.2, less than or equal to about 1:1.5, less than or equal to about 1:2, less than or equal to about 1:3, or less than or equal to about 1:5. In such circumstances, component (a) can be the limiting reactant in the process for producing the asymmetrical sulfide compound having formula (II) and/or the process for producing the asymmetrical ether compound having formula (I). Typical non-limiting ranges for the molar ratio of component (a) to component (b), therefore, can include from about 1:1.2 to about 1:15, from about 1:1.5 to about 1:10, from about 1:1.5 to about 1:6, from about 1:2 to about 1:10, from about 1:4 to about 1:20, or from about 1:2 to about 1:6. It should be noted that an excess of component (b) can promote greater yield of the asymmetrical sulfide and/or the asymmetrical ether. For instance, in the third process and the fifth process, the limiting reactant can be component (a)—the symmetrical sulfide compound. Likewise, in the fourth process and the sixth process, the limiting reactant can be component (a)—the symmetrical ether compound.

Optionally, the processes for producing an asymmetrical sulfide compound can further include an additional sulfur-containing reactant. That is, the process can comprise contacting component (a), component (b), the catalyst (c), and a sulfur-containing compound (d). Illustrative and non-limiting examples of the sulfur-containing compound include $H_2S$, $CS_2$, di-tert-butyl polysulfide, and the like, as well as any combination thereof. While not wishing to be bound by the following theory, it is believed that small amounts of such sulfur-containing materials can improve the yield of the asymmetrical sulfide compound. Any suitable amount of the sulfur-containing compound can be used, from an amount greater than zero and typically less than or equal to about 5 mol %. More often, the addition amount can be less than or equal to about 3 mol %, or less than or equal to about 1 mol %. These mole percentages are based on the moles of the limiting reactant. The di-tert-butyl polysulfide material is low in odor and non-volatile, and therefore can be conveniently used in the disclosed processes.

The processes described herein result in an unexpectedly high conversion of the limiting reactant and/or yield to the sulfide compound having formula (II) or to the ether compound having formula (I). In one aspect, the minimum conversion (or yield) can be at least about 50%, at least about 60%, at least about 70%, at least about 80%, at least about 90%, or at least about 95%. Additionally, the maximum conversion (or yield) can be about 97%, about 98%, about 99%, or about 99.5%, and can approach 100% conversion of the limiting reactant (or yield of the asymmetrical sulfide and/or the asymmetrical ether). Generally, the conversion (or yield) can be in a range from any minimum conversion (or yield) disclosed herein to any maximum conversion (or yield) disclosed herein. Non-limiting ranges of conversion (or yield) can include from about 50% to about 99.5%, from about 80% to about 99%, from about 90% to about 98%, or from about 95% to 100%. For conversion, the percentages are the amount of the limiting reactant converted based on the initial amount of the limiting reactant. The yield values are mole percentages, and are based on the moles of the sulfide compound having formula (II) produced (or based on the moles of the ether compound having formula (I) produced) to moles of the limiting reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor).

Also unexpectedly, continuous flow processes for producing the asymmetrical sulfide and/or the asymmetrical ether in accordance with this invention have unexpectedly high single pass conversions of the limiting reactant (or single pass yields to the desired asymmetrical sulfide and/or the desired asymmetrical ether). In one aspect, the minimum single pass conversion (or yield) can be at least about 40%, at least about 50%, at least about 60%, at least about 70%, or at least about 80%. Additionally, the maximum single pass conversion (or yield) can be about 90%, about 95%, about 98%, or about 99%, and can approach 100% conversion of the limiting reactant (or yield of the asymmetrical sulfide and/or the asymmetrical ether), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from about 40% to about 90%, from about 50% to about 95%, from about 60% to about 98%, or from about 70% to 100%.

The processes to produce asymmetrical sulfide and/or asymmetrical ether compounds disclosed herein typically result in a crude reaction mixture containing the asymmetrical sulfide and/or the asymmetrical ether, residual reactants, and relatively minor amounts of byproducts (e.g., mercaptans, sulfide heavies). Beneficially, and unexpectedly, the amount of mercaptan reaction products (such as methyl mercaptan and/or ethyl mercaptan when dimethyl sulfide and diethyl sulfide are the reactants) in the reaction mixture is very low. For instance, in one aspect, the reaction mixture can contain less than or equal to about 5 wt. % mercaptan reaction products (or less than or equal to about 5 wt. % methyl mercaptan, or less than or equal to about 5 wt. % ethyl mercaptan), while in another aspect, the reaction mixture can contain less than or equal to about 3 wt. % mercaptan reaction products (or less than or equal to about 3 wt. % methyl mercaptan, or less than or equal to about 3 wt. % ethyl mercaptan), and in yet another aspect, the reaction mixture can contain less than or equal to about 2 wt. % (or 1 wt. %) mercaptan reaction products (or less than or equal to about 2 wt. % (or 1 wt. %) methyl mercaptan, or less than or equal to about 2 wt. % (or 1 wt. %) ethyl mercaptan).

In many instances, it can be desirable to isolate the asymmetrical sulfide and/or the asymmetrical ether from the reaction mixture for sale or for use in further industrial processes. Accordingly, in certain aspects, the process for producing an asymmetrical sulfide and/or an asymmetrical ether can further comprise a step of isolating the sulfide compound having formula (II) (or isolating the ether compound having formula (I)) from the reaction mixture to form a product stream containing the sulfide compound having formula (II) (or a product stream containing the ether compound having formula (I)). Isolation of the sulfide compound having formula (II) (or the ether compound having formula (I)) can employ any suitable technique for separating the sulfide compound having formula (II) (or the ether compound having formula (I)) from other components of the reaction mixture, in order to form a product stream containing the sulfide compound having formula (II) (or the ether compound having formula (I)). Such techniques can include, but are not limited to, extraction, filtration, evaporation, or distillation, as well as combinations of two or more of these techniques. In particular aspects of this invention, the isolating step utilizes distillation at any suitable pressure (one or more than one distillation column can be used). Advantageously, the low levels of mercaptans in the reaction mixture make isolating, for instance, an asymmetrical sulfide such as methyl ethyl sulfide via distillation a relatively straightforward process.

Additionally, other components of the reaction mixture (e.g., component (a) and component (b)) can be recovered and recycled to the reactor. In such instances, the limiting reactant can be recycled to extinction, such that all or substantially all (>99 mol %) of the limiting reactant is converted to the sulfide compound having formula (II) (or to the ether compound having formula (I)), or to a byproduct.

After isolating, and unexpectedly, the processes to produce asymmetrical sulfides and/or asymmetrical ethers disclosed herein can result in a high yield of the sulfide compound having formula (II) (or the ether compound having formula (I)) in the product stream. Generally, the sulfide compound having formula (II) (or the ether compound having formula (I)) can be produced in a yield of at least about 40 mol %, and more often, at least about 50 mol %, at least about 60 mol %, at least about 70 mol %, or at least about 80 mol %, and often as high as 90-100 mol %, in the product stream. This yield is based on the moles of the limiting reactant. Generally, purification steps to isolate a desired product from a crude reaction mixture reduce the overall yield of the desired product. However, consistent with this invention, the isolated asymmetrical sulfide and/or the isolated asymmetrical ether can be recovered in a yield similar to that of the crude asymmetrical sulfide and/or the crude asymmetrical ether.

After the isolating step, the sulfide compound having formula (II) (or the ether compound having formula (I)) can have a purity of at least about 80 wt. %, at least about 85 wt. %, at least about 90 wt. %, at least about 95 wt. %, or at least about 98 wt. %, in the product stream. The purity is based on the weight of the sulfide compound having formula (II) (or the ether compound having formula (I)) in the product stream to the total weight of the product stream.

The catalyst compositions used in the processes disclosed herein are not particularly limited, so long as they are able to promote a reaction between component (a) and component (b) to produce an asymmetrical sulfide and/or an asymmetrical ether, as described herein. In one aspect, the catalyst can comprise any suitable solid hydrotreating catalyst. In another aspect, the catalyst can comprise a CoMo catalyst, a NiMo catalyst, and the like, as well as any combination thereof. In yet another aspect, the catalyst (e.g., the CoMo and/or NiMo catalyst) can be pre-sulfided to increase the conversion of the limiting reactant and the yield of the asymmetrical sulfide and/or the asymmetrical ether.

As would be recognized by one of skill in the art, the catalyst can be supported on any suitable solid oxide or like material. Thus, the catalyst can further comprise a support or solid oxide, illustrative examples of which can include silica, alumina, silica-alumina, aluminum phosphate, zinc aluminate, zirconia, thoria, and the like. Combinations of more than one support material can be used for the catalyst.

Consistent with another aspect of this invention, the catalyst does not contain a transition metal. For instance, the catalyst can comprise (or consist essentially of, or consist of) γ-alumina in one aspect of this invention. In another aspect, the catalyst can comprise a molecular sieve or a zeolite (a crystalline aluminosilicate), such as a Y-zeolite (zeolite Y) or a X-zeolite (zeolite X). Zeolites can exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, hydrogen, or combinations thereof.

The Y-zeolite (zeolite Y) and X-zeolite (zeolite X) can have an average pore diameter in a range of from about 7 Å to about 12 Å. The Si:Al ratio for a X-zeolite is less than that for a Y-zeolite. Often, the zeolite can be bound with a support matrix (or binder), non-limiting examples of which can include silica, alumina, magnesia, boria, titania, zirconia, various clays, and the like, including mixed oxides thereof, as well as mixtures thereof.

In some aspects, the catalyst can comprise supported CoMo and an alkali or alkaline earth metal hydroxide, such as described in U.S. Pat. No. 4,277,623, incorporated herein by reference in its entirety. For instance, the catalyst can contain 3-4 wt. % cobalt oxide and 15-16 wt. % molybdenum oxide supported on alumina, although the respective amounts of Co and Mo are not limited thereto. Illustrative examples of suitable hydroxides can include, but are not limited to, lithium hydroxide, sodium hydroxide, potassium hydroxide, rubidium hydroxide, cesium hydroxide, magnesium hydroxide, calcium hydroxide, barium hydroxide, and the like, as well as combinations thereof. The hydroxide component can be in any form, but beneficially for the processes disclosed herein, can be in pellet form for use in a fixed or packed bed reactor configuration. The relative amounts of the supported CoMo component and the hydroxide component are not particularly limited, although an excess of the hydroxide component, on a weight basis, often can be used.

In some aspects, the catalyst can comprise a metal salt compound, typically palladium (II), rhodium (III), platinum (II), and/or copper (I) or (II) salt compounds, as described in U.S. Pat. No. 4,005,129, incorporated herein by reference in its entirety. The catalyst also can include an aliphatic, cycloaliphatic, aromatic, or heterocyclic amine or ammonia, as well as copper (II) or iron (III) oxidant compounds—e.g., a copper (II) oxalate, sulfate, acetate, or trifluoroacetate oxidant salt compound. Representative metal salt compounds can include, but are not limited to, palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, and the like, as well as combinations thereof. Any or all of the catalyst components can be supported on any suitable support material or solid oxide.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 7890A GC System, using an HP-5 column (dimethylpolysiloxane, capillary 30 m×0.32 μm×0.25 μm nominal), with 35° C. temperature hold for 5 min followed by ramping at a rate of 5° C./min from 35° C. to 70° C., followed by ramping at 10° C./min to 260° C., then holding at 260° C. for 10 min. Standards for dimethyl sulfide (DMS), diethyl sulfide (DES), dioctyl sulfide (DOS), methyl ethyl sulfide (YMS), ethyl n-octyl sulfide (ENOS), diethyl ether (DEE), and methanol were used to identify the respective reactants and products. Product composition information is presented in area percentages (area %), unless otherwise specified.

Examples 1-16

Synthesis of an Asymmetrical Sulfide Compound (Methyl Ethyl Sulfide) from Symmetrical Sulfide Compounds For Example 1, dimethyl sulfide (DMS) and diethyl sulfide (DES) were blended in a feed tank at an approximate weight ratio of 4:1 (DMS:DES), which was confirmed via GC. FIG. 1 is a GC plot of the blended feed containing DMS and DES. The respective amounts of DMS (eluting at 11 min; 79.3%) and DES (eluting at 18 min; 20.7%) via area percentages are listed in Table I.

The DMS and DES blend was fed into the top of a fixed bed reactor containing a mixed bed of (i) supported CoMo on alumina and (ii) γ-alumina at a total flow rate (DMS and DES) of 17 g/hr. The WHSV was 0.1 (weight of DES which comes in contact with the catalyst per unit time, in g/g/hr). The fixed bed reactor had three independent heating zones: the top zone of the reactor (5.71 g of γ-alumina and 6.85 g of supported CoMo), the middle zone of the reactor (8.41 g of γ-alumina and 3.31 g of supported CoMo), and the bottom zone of the reactor (10.7 g of γ-alumina). As shown in Table I, the reaction temperature was approximately 270-300° C., and the reaction pressure was 300 psig (2068 kPag). Unexpectedly, 90% of the DES was converted, primarily to methyl ethyl sulfide (MES).

Figure 2:
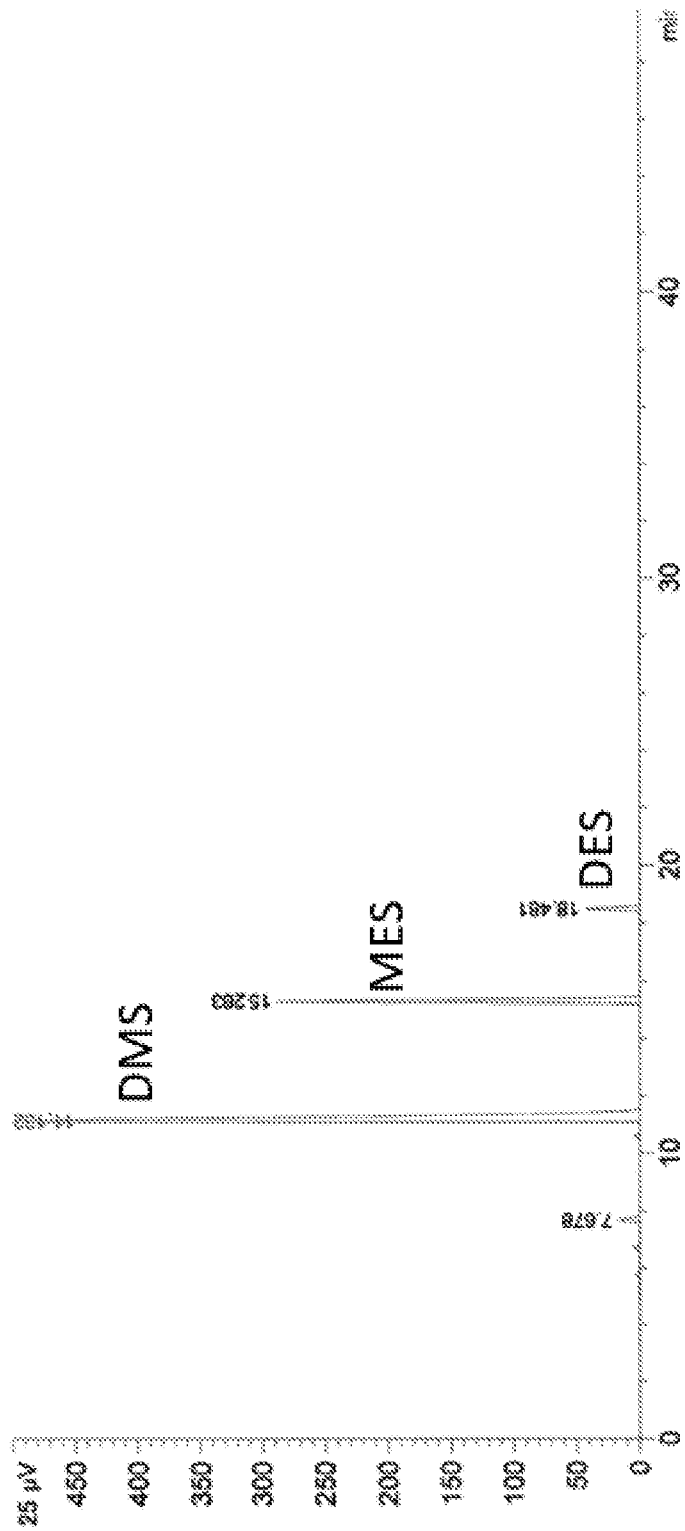
FIG. 2 presents a gas chromatograph plot of the reaction mixture of Example 3 containing methyl ethyl sulfide.

The same general procedure was used for Examples 2-4, and the results are summarized in Table I, with the respective amounts of DMS, DES, and MES in area percentages. The percent conversions of DMS, primarily to MES, were in the 70-80% range. FIG. 2 is a GC plot of the reaction mixture of Example 3, with DMS eluting at 11 min (~67 area %), DES eluting at 18 min (~4.5 area %), and MES eluting at 15 min (~25 area %).

For Examples 5-9, the same general procedure for Example 1 was followed, except that the top zone of the reactor contained 6.92 of inert alumina and 6.90 g of supported CoMo, the middle zone of the reactor contained 3.82 g of inert alumina and 9.47 g of supported CoMo, and the bottom zone of the reactor contained 13.22 g of supported CoMo. The results are summarized in Table I. Generally, the lower reaction temperatures used in Examples 5-9 resulted in significantly lower conversions of DES.

Figure 3:
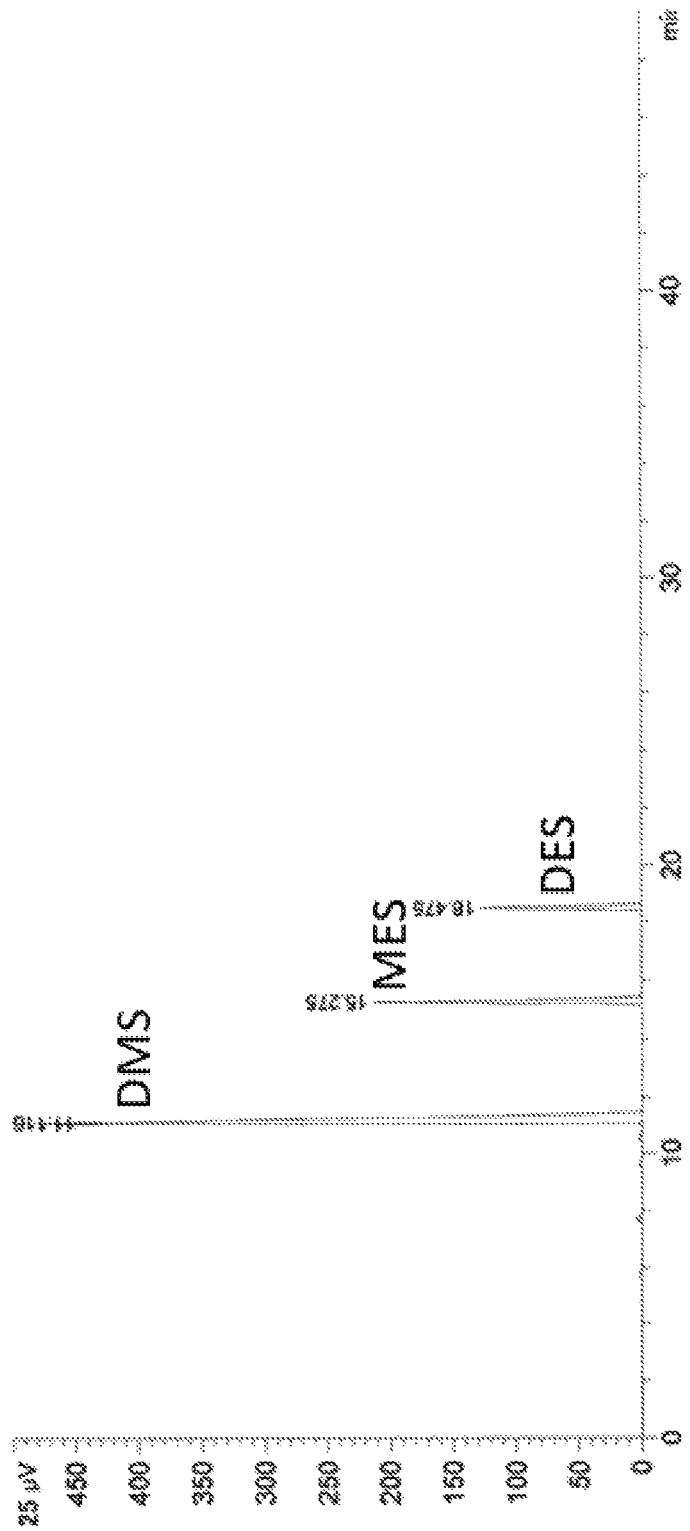
FIG. 3 presents a gas chromatograph plot of a reaction mixture containing methyl ethyl sulfide, produced using a CoMo catalyst.

For Examples 10-13, the same general procedure for Examples 5-9 was followed. The results are summarized in Table I. The reaction temperatures for Examples 11-13 were in the 270-380° C. range and, unexpectedly, 88-91% of the DES was converted, primarily to methyl ethyl sulfide (YMS). FIG. 3 is a GC plot of a reaction mixture representative of Examples 5-13, with DMS eluting at 11 min, DES eluting at 18 min, and MES eluting at 15 min.

For Example 14, dimethyl sulfide (DMS) and diethyl sulfide (DES) were blended in a feed tank at an approximate weight ratio of 4:1 (DMS:DES), along with approximately 4.7 wt. % of TBPS 454 di-tert-butyl polysulfide (CAS No. 68937-96-2), based on the total weight of the blended feed. While not wishing to be bound by the following theory, it is believed that the TBPS 454 may decompose to free mercaptan and help initiate the reaction to produce IViES. The blended feed was fed into the top of the fixed bed reactor containing only γ-alumina (33.5 g) at a WHSV of 0.2 (weight of DES which comes in contact with the catalyst per unit time, in g/g/hr). The results are summarized in Table I. Unexpectedly, in Example 14, 80% of the DES was converted using only γ-alumina (no CoMo or NiMo), primarily to methyl ethyl sulfide (YMS).

Figure 4:
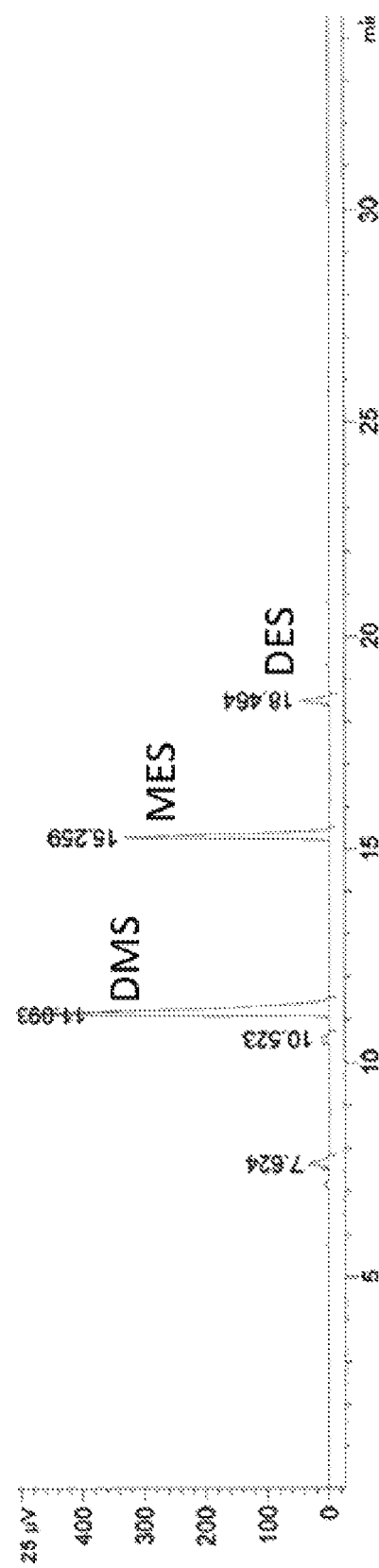
FIG. 4 presents a gas chromatograph plot of a reaction mixture containing methyl ethyl sulfide, produced using a γ-alumina catalyst.

For Example 15, the same general procedure for Example 14 was followed, except that the flow rate was reduced to result in a WHSV of 0.1 (see Table I). Unexpectedly, 87% of the DES was converted using only γ-alumina (no CoMo or NiMo), primarily to methyl ethyl sulfide (YMS). FIG. 4 is a GC plot of a reaction mixture representative of Examples 14-15, with DMS eluting at 11 min, DES eluting at 18 min, and MES eluting at 15 min.

Beneficially, and unexpectedly, few by-products were observed in Examples 1-15, and thus purification of the crude MES product would not be problematic. Also surprisingly, only a small amount of methyl mercaptan (MeSH) was present in the reactor effluent; MeSH concentrations were approximately ~0.5-3 wt. % in the reactor effluent, regardless of the catalyst used. Ethyl mercaptan was present at much less than 1 wt. % in the reactor effluent, and often not detectable.

For Example 16, the conditions of Example 14 were utilized, except that the feed ratio of dimethyl sulfide (DMS) and diethyl sulfide (DES) was reversed, such that DMS was the limiting reactant. The molar ratio of DES:DMS was 5:1 in Example 16. Similar to Examples 1-15, MES was produced in Example 16.

Example 17

Figure 5:
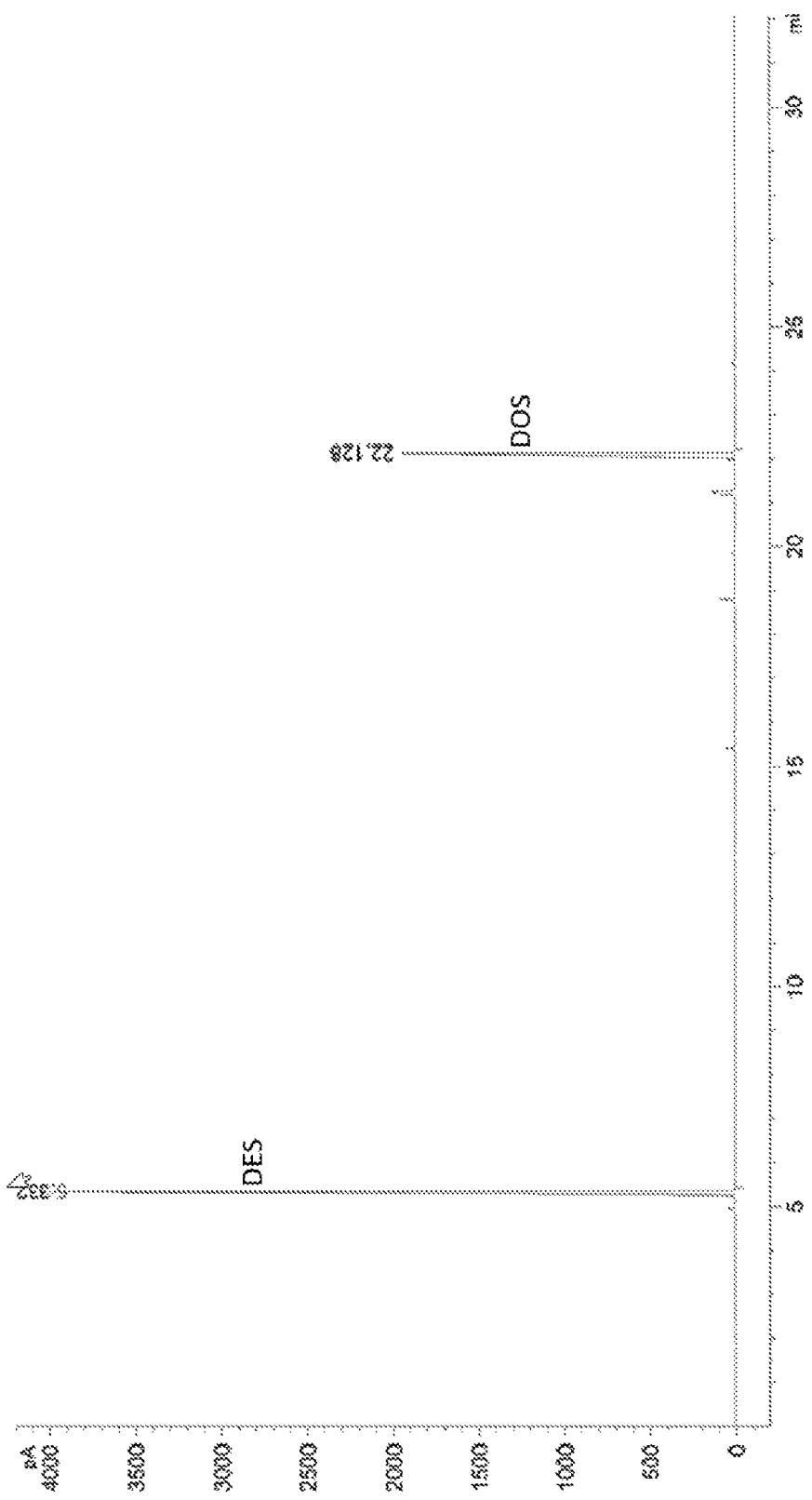
FIG. 5 presents a gas chromatograph plot of the blended feed of diethyl sulfide and dioctyl sulfide used in Example 17.
Figure 6:
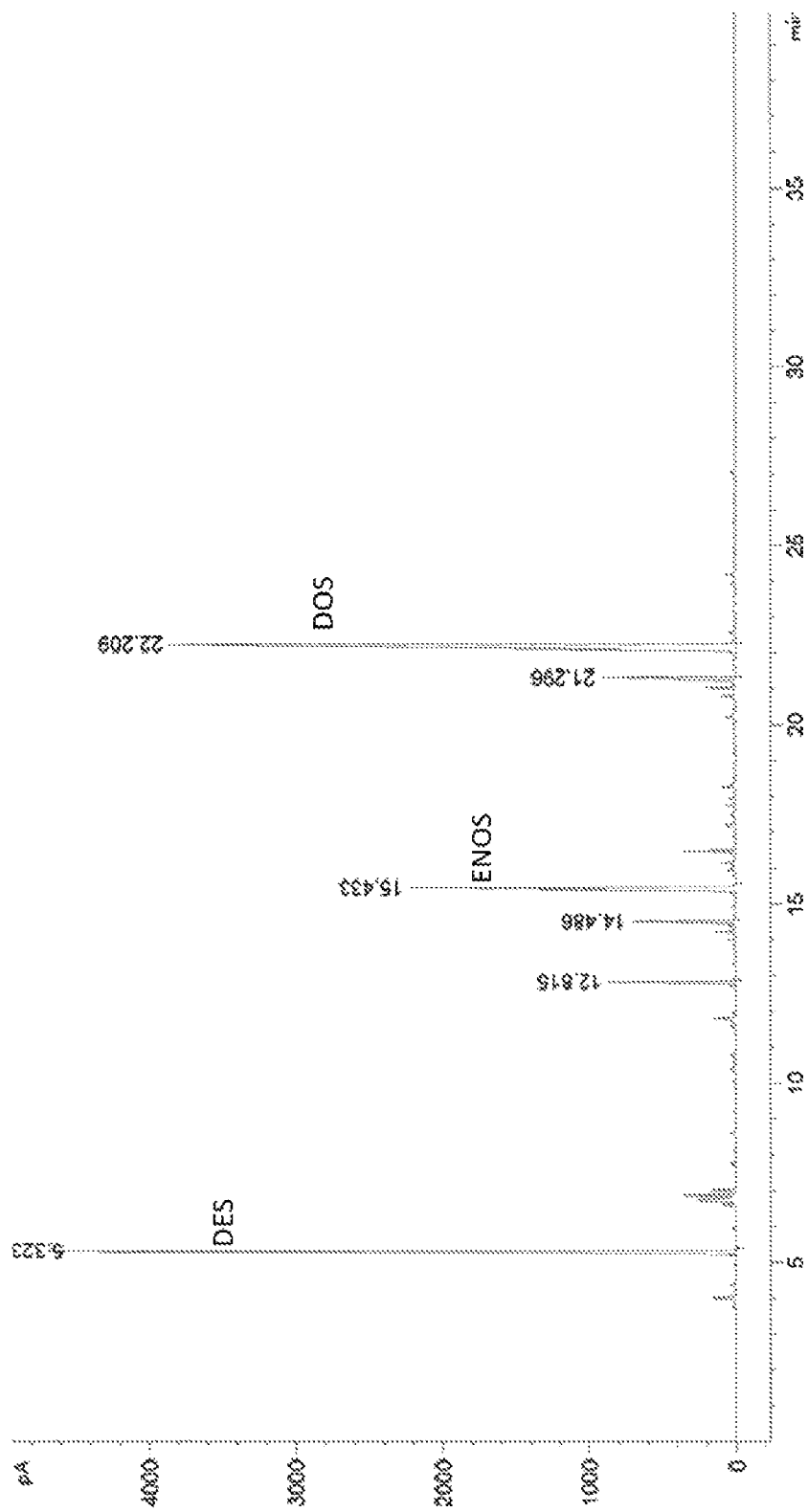
FIG. 6 presents a gas chromatograph plot of the reaction mixture of Example 17 containing ethyl n-octyl sulfide.

Synthesis of an Asymmetrical Sulfide Compound (ethyl N-Octyl Sulfide) from Symmetrical Sulfide Compounds Example 17 was performed similarly to that of Examples 14-15. Diethyl sulfide (DES) and dioctyl sulfide (DOS) were blended in a feed tank at an approximate molar ratio of 5:1 (DES:DOS), along with approximately 3.3 wt. % of TBPS 454 di-tert-butyl polysulfide (CAS No. 68937-96-2), based on the total weight of the blended feed. The blended feed was fed into the top of the fixed bed reactor containing only γ-alumina (33.5 g) at 315° C. and a WHSV of 0.5 (weight of DOS which comes in contact with the catalyst per unit time, in g/g/hr). FIG. 5 is a GC plot of the blended feed containing DES (eluting at 5.3 min) and DOS (eluting at 22 min). Unexpectedly, in Example 17, approximately 80% of the DOS was converted using only γ-alumina (no CoMo or NiMo). The reaction mixture contained about 13.6 wt. % ethyl n-octyl sulfide (ENOS). FIG. 6 is a GC plot of a reaction mixture of Example 17, with DES eluting at 5.3 min, ENOS eluting at 15.4 min, and DOS eluting at 22 min.

Example 18

Figure 7:
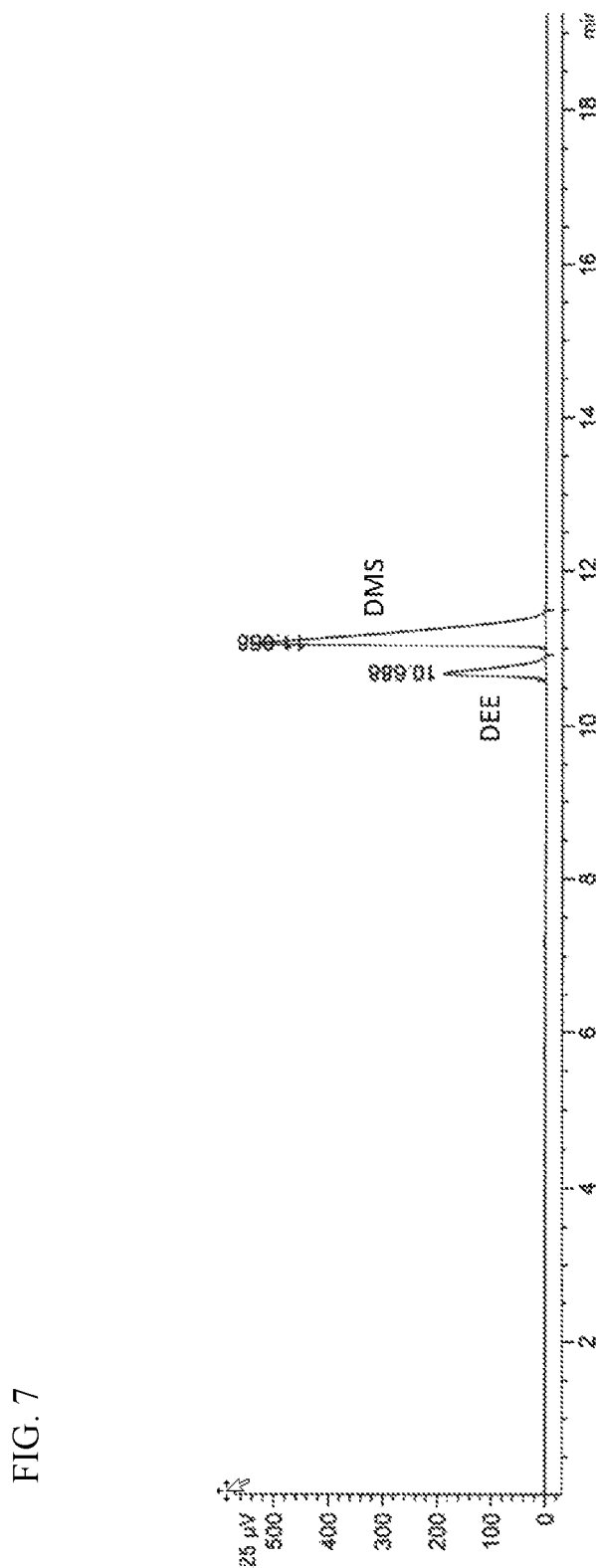
FIG. 7 presents a gas chromatograph plot of the blended feed of dimethyl sulfide and diethyl ether used in Example 18.

Synthesis of an Asymmetrical Sulfide Compound (Methyl Ethyl Sulfide) and an Asymmetrical Ether Compound (Methyl Ethyl Ether) from Symmetrical Sulfide and Ether Compounds For Example 18, dimethyl sulfide (DMS) and diethyl ether (DEE) were blended in a feed tank at an approximate molar ratio of 5:1 (DMS:DEE), which was confirmed via GC, along with approximately 4.7 wt. % of TBPS 454 di-tert-butyl polysulfide (CAS No. 68937-96-2), based on the total weight of the blended feed. While not wishing to be bound by the following theory, it is believed that the TBPS 454 may decompose to free mercaptan and help initiate the reaction to produce MES. FIG. 7 is a GC plot of the blended feed containing DMS (eluting at 11.068 min) and DEE (eluting at 10.688 min).

Figure 8:
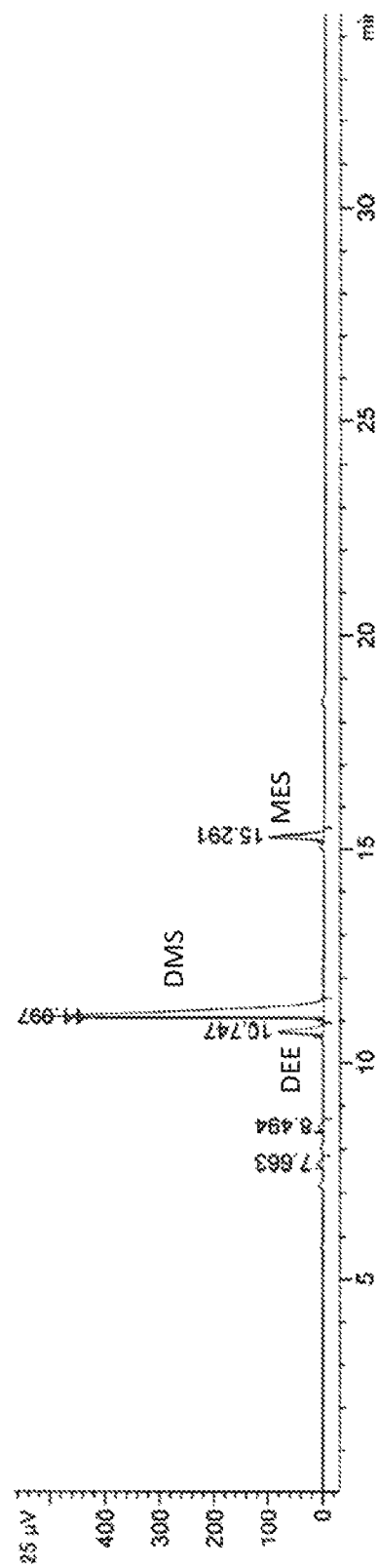
FIG. 8 presents a gas chromatograph plot of the reaction mixture of Example 18 containing methyl ethyl sulfide.

The DMS and DEE blend was fed into the top of a fixed bed reactor containing a bed of presulfided ½oth inch pelleted catalyst (supported CoMo on alumina). The WHSV was 1.0 (weight of total mixed feed which comes in contact with the catalyst per unit time, in g/g/hr). The reaction temperature was 300° C. and the reaction pressure was 300 psig (2068 kPag). Unexpectedly, in the absence of any halides, there was 61% conversion of DEE. FIG. 8 is a GC plot of the reactor effluent mixture of Example 18, with the asymmetrical sulfide (MES) eluting at 15.291 min.

This example demonstrates the synthesis of an asymmetrical sulfide compound (methyl ethyl sulfide) in high yield, from symmetrical sulfide and ether compounds, in a water-free and low corrosion process. Beneficially, the reactants and catalyst contain no halides (chlorides).

Example 19

Figure 9:
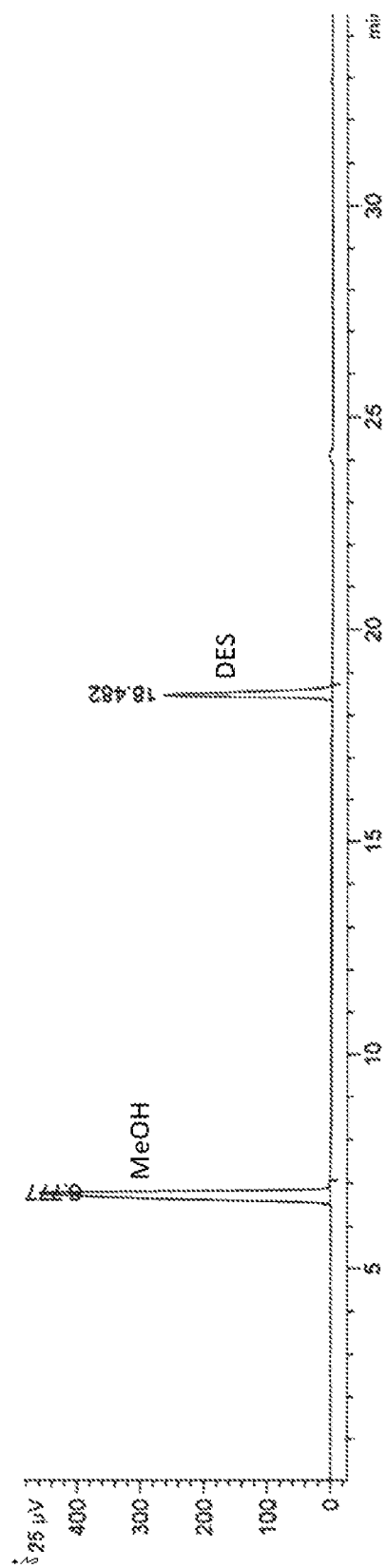
FIG. 9 presents a gas chromatograph plot of the blended feed of diethyl sulfide and methanol used in Example 19.

Synthesis of an Asymmetrical Sulfide Compound (Methyl Ethyl Sulfide) from a Symmetrical Sulfide Compound and an Alcohol Compound For Example 19, methanol and dimethyl sulfide (DES) were blended in a feed tank at an approximate molar ratio of 3:1 (methanol:DES), which was confirmed via GC, along with approximately 4.7 wt. % of TBPS 454 di-tert-butyl polysulfide (CAS No. 68937-96-2), based on the total weight of the blended feed. While not wishing to be bound by the following theory, it is believed that the TBPS 454 may decompose to free mercaptan and help initiate the reaction to produce MES. FIG. 9 is a GC plot of the blended feed containing methanol (eluting at 6.78 min) and DES (eluting at 18.48 min).

The methanol and DES blend was fed into the top of a fixed bed reactor containing a bed of presulfided ½oth inch pelleted catalyst (supported CoMo on alumina). The WHSV was 1.0 (total weight of methanol and DES which comes in contact with the catalyst per unit time, in g/g/hr). The reaction temperature was 300° C. and the reaction pressure was 300 psig (2068 kPag). The reactor effluent mixture was a two-phase mixture of liquids at standard temperature and pressure. Unexpectedly, in the absence of any chlorides or halides, a significant amount of the DES was converted to methyl ethyl sulfide (YMS).

Figure 10:
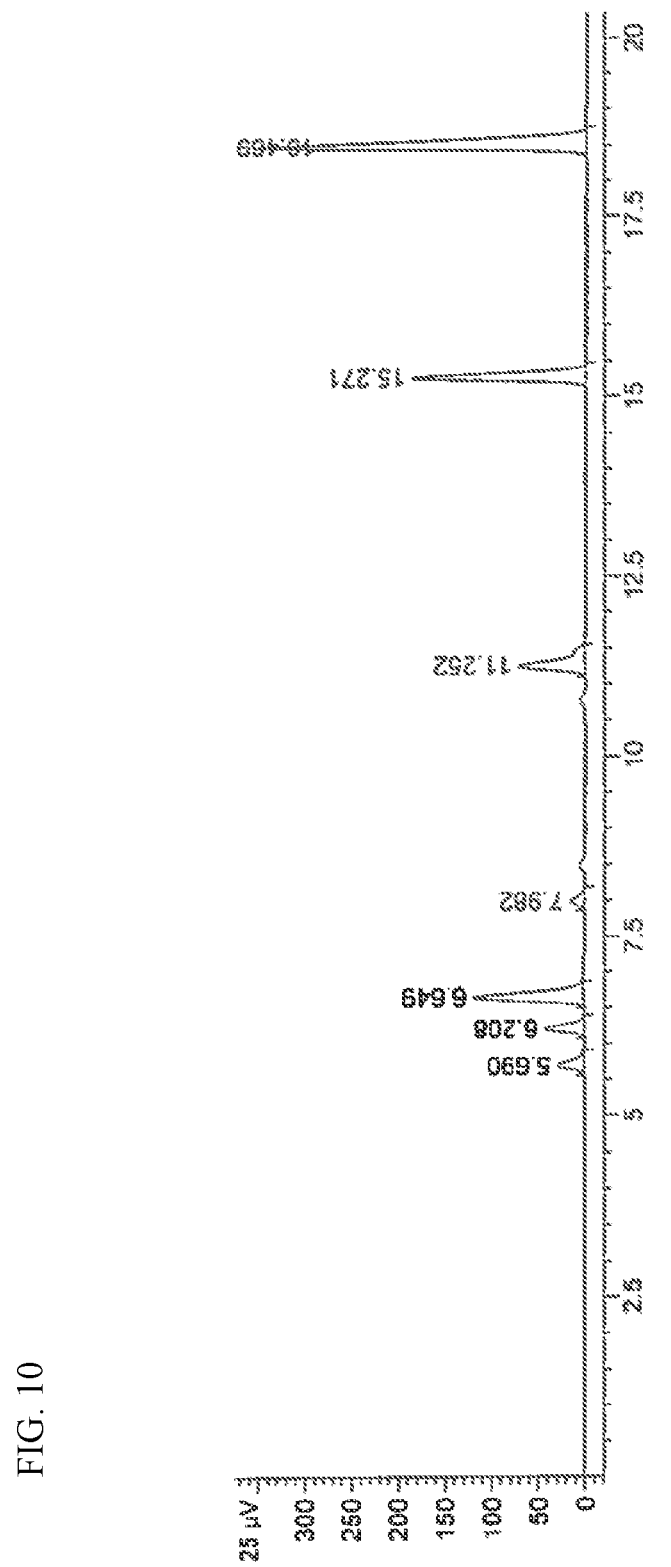
FIG. 10 presents a gas chromatograph plot of the top phase of the reaction mixture of Example 19 containing methyl ethyl sulfide.
Figure 11:
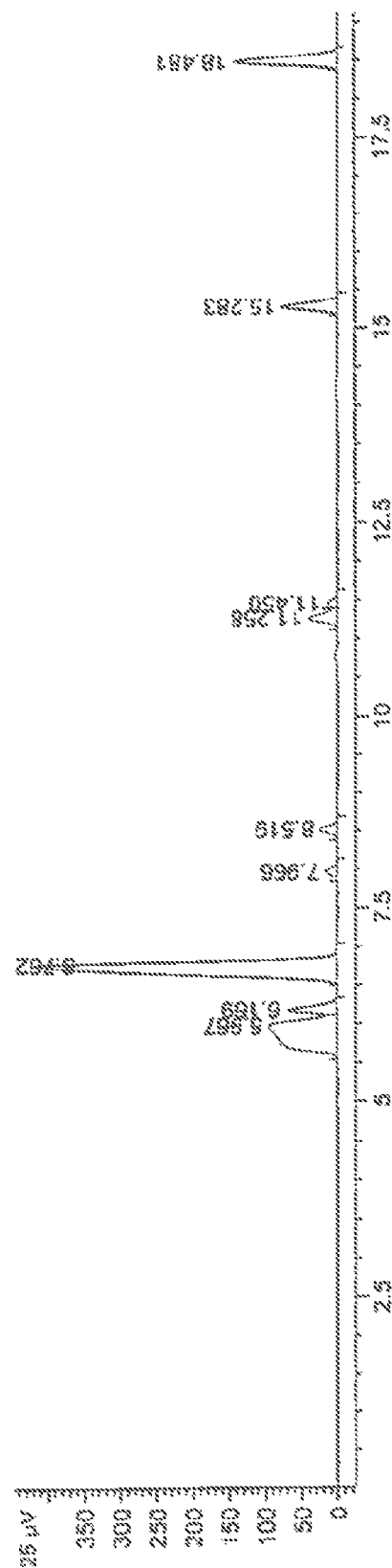
FIG. 11 presents a gas chromatograph plot of the bottom phase of the reaction mixture of Example 19.

FIG. 10 is a GC plot of the top phase of the reactor effluent mixture of Example 19, with the asymmetrical sulfide (MES) eluting at 15.27 min. In FIG. 10, the area percentages are as follows: methanol (14.6%), MES (29.3%), and DES (45.3%). FIG. 11 is a GC plot of the bottom phase of the reactor effluent mixture of Example 19 containing water. In FIG. 11, the area percentages are as follows: water (22.4%), methanol (48%), MES (5.5%), and DES (11.4%).

This example demonstrates the synthesis of an asymmetrical sulfide compound (methyl ethyl sulfide) in high yield, from a symmetrical sulfide and an alcohol compound. This synthesis scheme can replace methods of making asymmetrical sulfides which utilize UV reactions or halide displacement.

TABLE I

Summary of Examples 1-15.

| Example | WHSV | Top (° C.) | Middle (° C.) | Bottom (° C.) | Flowrate (g/hr) | Pressure (psig) | DMS (%) | MES (%) | DES (%) | DES Conversion (%) |
|---|---|---|---|---|---|---|---|---|---|---|
| Feed | — | — | — | — | — | — | 79.30 | 0.00 | 20.70 | — |
| 1 | 0.10 | 269 | 301 | 296 | 17 | 301 | 49.13 | 17.82 | 1.97 | 90.5 |
| 2 | 0.10 | 294 | 309 | 304 | 17 | 295 | 67.87 | 26.50 | 3.93 | 81.0 |
| 3 | 0.10 | 294 | 301 | 298 | 17 | 300 | 67.41 | 25.36 | 4.51 | 78.2 |
| 4 | 0.05 | 292 | 302 | 298 | 9 | 298 | 68.16 | 23.40 | 5.88 | 71.6 |
| 5 | 0.10 | 261 | 149 | 107 | 15 | 313 | 68.65 | 4.87 | 11.66 | 43.7 |
| 6 | 0.10 | 272 | 143 | 99 | 15 | 310 | 68.68 | 16.90 | 8.69 | 58.0 |
| 7 | 0.42 | 200 | 139 | 29 | 60 | 308 | 67.04 | 20.18 | 12.78 | 38.2 |

TABLE I-continued

Summary of Examples 1-15.

| Example | WHSV | Top (° C.) | Middle (° C.) | Bottom (° C.) | Flowrate (g/hr) | Pressure (psig) | DMS (%) | MES (%) | DES (%) | DES Conversion (%) |
|---|---|---|---|---|---|---|---|---|---|---|
| 8 | 0.42 | 291 | 188 | 148 | 60 | 294 | 73.52 | 9.67 | 15.44 | 25.4 |
| 9 | 0.42 | 292 | 190 | 154 | 60 | 294 | 73.45 | 9.82 | 15.37 | 25.7 |
| 10 | 0.10 | 333 | 179 | 122 | 15 | 303 | 72.92 | 15.13 | 10.02 | 51.6 |
| 11 | 0.10 | 340 | 381 | 340 | 15 | 303 | 60.83 | 17.95 | 2.46 | 88.1 |
| 12 | 0.10 | 281 | 286 | 269 | 15 | 298 | 64.24 | 25.84 | 2.12 | 89.7 |
| 13 | 0.10 | 299 | 306 | 297 | 15 | 300 | 65.66 | 25.54 | 2.01 | 90.3 |
| 14 | 0.20 | 297 | 282 | 199 | 33 | 318 | 60.99 | 30.61 | 4.08 | 80.3 |
| 15 | 0.10 | 299 | 281 | 185 | 17 | 308 | 62.49 | 28.57 | 2.74 | 86.8 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for producing an ether or sulfide compound having formula (III):

$$R^1—X—R^2 \quad (III);$$

the process comprising contacting:
(a) a first ether or sulfide compound having formula (F), $$R^1—X—R^1 \quad (F);$$

(b) a second ether or sulfide compound having formula (G), $$R^2—X—R^2 \quad (G); \text{ and}$$

(c) a catalyst;
to form a reaction mixture comprising the ether or sulfide compound having formula (III); wherein:
each X independently is sulfur or oxygen;
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 2. A process for producing an ether or sulfide compound having formula (III):

$$R^1—X—R^2 \quad (III);$$

the process comprising contacting:
(a) an ether or sulfide compound having formula (F), $$R^1—X—R^1 \quad (F);$$

(b) an alcohol or thiol compound having formula (H), $$R^2—XH \quad (H); \text{ and}$$

(c) a catalyst;
to form a reaction mixture comprising the ether or sulfide compound having formula (III); wherein:
each X independently is sulfur or oxygen;
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 3. A process for producing an ether compound having formula (I):

$$R^1—O—R^2 \quad (I);$$

the process comprising contacting:
(a) a first ether compound having formula (A), $$R^1—O—R^1 \quad (A);$$

(b) a second ether compound having formula (B), $$R^2—O—R^2 \quad (B); \text{ and}$$

(c) a catalyst;
to form a reaction mixture comprising the ether compound having formula (I); wherein:
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 4. A process for producing a sulfide compound having formula (II) and an ether compound having formula (I):

$$R^1—S—R^2 \quad (II)$$

$$R^1—O—R^2 \quad (I);$$

the process comprising contacting:
(a) an ether compound having formula (B), $$R^2—O—R^2 \quad (B);$$

(b) a sulfide compound having formula (C), $$R^1—S—R^1 \quad (C); \text{ and}$$

(c) a catalyst;
to form a reaction mixture comprising the sulfide compound having formula (II) and the ether compound having formula (I); wherein:
$R^1$—is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 5. A process for producing a sulfide compound having formula (II):

$$R^1—S—R^2 \quad (II);$$

the process comprising contacting:
(a) a sulfide compound having formula (C), $$R^1—S—R^1 \quad (C);$$

(b) an alcohol compound having formula (D), $$R^2—OH \quad (D); \text{ and}$$

(c) a catalyst;
to form a reaction mixture comprising the sulfide compound having formula (II); wherein:
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 6. A process for producing an ether compound having formula (I):

$$R^1\text{—}O\text{—}R^2 \quad (I);$$

the process comprising contacting:
(a) an ether compound having formula (A), $$R^1\text{—}O\text{—}R^1 \quad (A);$$

(b) an alcohol compound having formula (D), $$R^2\text{—}OH \quad (D); \text{ and}$$

(c) a catalyst;
to form a reaction mixture comprising the ether compound having formula (I); wherein:
$R^1$—is a $C_1$ to $C_{18}$ substituted or unsubstituted, cycloalkyl group or linear or branched alkyl group; and
$R^2$ is a $C_1$ to $C_{18}$ is substituted or unsubstituted, cycloalkyl group or linear or branched alkyl group.

Aspect 7. A process for producing a sulfide compound having formula (II):

$$R^1\text{—}S\text{—}R^2 \quad (II);$$

the process comprising contacting:
(a) a sulfide compound having formula (C), $$R^1\text{—}S\text{—}R^1 \quad (C);$$

(b) a thiol compound having formula (E), $$R^2\text{—}SH \quad (E); \text{ and}$$

(c) a catalyst;
to form a reaction mixture comprising the sulfide compound having formula (II); wherein:
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 8. A process for producing a sulfide compound having formula (II):

$$R^1\text{—}S\text{—}R^2 \quad (II);$$

the process comprising contacting:
(a) an ether compound having formula (A), $$R^1\text{—}O\text{—}R^1 \quad (A);$$

(b) a thiol compound having formula (E), $$R^2\text{—}SH \quad (E); \text{ and}$$

(c) a catalyst;
to form a reaction mixture comprising the sulfide compound having formula (II); wherein:
$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 9. A process for producing a sulfide compound having formula (II):

$$R^1\text{—}S\text{—}R^2 \quad (II);$$

the process comprising contacting:
(a) a first sulfide compound having formula (C), $$R^1\text{—}S\text{—}R^1 \quad (C);$$

(b) a second sulfide compound having formula (J), $$R^2\text{—}S\text{—}R^2 \quad (J); \text{ and}$$

(c) a catalyst;
to form a reaction mixture comprising the sulfide compound having formula (II); wherein:

$R^1$ is a $C_1$ to $C_{18}$ substituted or unsubstituted, cycloalkyl group or linear or branched alkyl group; and
$R^2$ is a $C_1$ to $C_{18}$ substituted or unsubstituted, cycloalkyl group or linear or branched alkyl group.

Aspect 10. The process defined in any one of aspects 1-9, wherein $R^1$ and $R^2$ are different.

Aspect 11. The process defined in any one of aspects 1-10, wherein $R^1$ is a branched alkyl group.

Aspect 12. The process defined in any one of aspects 1-10, wherein $R^1$ is a linear alkyl group.

Aspect 13. The process defined in any one of aspects 1-12, wherein $R^1$ is a substituted alkyl group (e.g., a phenyl-substituted alkyl group).

Aspect 14. The process defined in any one of aspects 1-13, wherein $R^1$ is a $C_1$ to $C_{12}$ alkyl group.

Aspect 15. The process defined in any one of aspects 1-10, wherein $R^1$ is a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group.

Aspect 16. The process defined in any one of aspects 1-10, wherein $R^1$ is a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, or a tert-amyl group.

Aspect 17. The process defined in any one of aspects 1-10, wherein $R^1$ is a methyl group or an ethyl group.

Aspect 18. The process defined in any one of aspects 1-17, wherein $R^2$ is a branched alkyl group.

Aspect 19. The process defined in any one of aspects 1-17, wherein $R^2$ is a linear alkyl group.

Aspect 20. The process defined in any one of aspects 1-19, wherein $R^2$ is a substituted alkyl group (e.g., a phenyl-substituted alkyl group).

Aspect 21. The process defined in any one of aspects 1-20, wherein $R^2$ is a $C_1$ to $C_{12}$ alkyl group.

Aspect 22. The process defined in any one of aspects 1-17, wherein $R^2$ is a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group.

Aspect 23. The process defined in any one of aspects 1-17, wherein $R^2$ is a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, or a tert-amyl group.

Aspect 24. The process defined in any one of aspects 1-17, wherein $R^2$ is a methyl group or an ethyl group.

Aspect 25. The process defined in any one of aspects 4, 5, 7, 8, or 9, wherein the sulfide compound having formula (II) is methyl ethyl sulfide, methyl iso-propyl sulfide, methyl dodecyl sulfide, ethyl octyl sulfide, or n-pentyl n-heptyl sulfide.

Aspect 26. The process defined in any one of aspects 3, 4, or 6, wherein the ether compound having formula (I) is methyl ethyl ether, methyl iso-propyl ether, methyl tert-butyl ether, or methyl tert-amyl ether.

Aspect 27. The process defined in any one of the preceding aspects, wherein the process comprises combining (a) and (b) prior to contacting (c) the catalyst.

Aspect 28. The process defined in any one of the preceding aspects, wherein the step of contacting is conducted at a temperature in any suitable range or any range disclosed herein, e.g., from about 200° C. to about 500° C., from about 125° C. to about 400° C., or from about 250° C. to about 350° C.

Aspect 29. The process defined in any one of the preceding aspects, wherein the step of contacting is conducted at a pressure in any suitable range or any range disclosed herein, e.g., from about 50 to about 850 psig (344 to 5860 kPag), from about 50 to about 500 psig (344 to 3447 kPag), or from about 150 to about 400 psig (1034 to 2758 kPag).

Aspect 30. The process defined in any one of the preceding aspects, wherein a molar ratio of (a) to (b)—molar ratio of (a):(b)—is in any suitable range or any range disclosed herein, e.g., from about 10:1 to about 1:10, from about 5:1 to about 1:5, or from about 2:1 to about 1:2.

Aspect 31. The process defined in any one of the preceding aspects, wherein (a) is a limiting reactant in the production of the sulfide compound having formula (II) (or the ether compound having formula (I), or the ether or sulfide compound having formula (III)).

Aspect 32. The process defined in any one of the preceding aspects, wherein a molar ratio of (a) to (b) is in any suitable range or any range disclosed herein, e.g., from about 1:1.5 to about 1:10, from about 1:4 to about 1:20, or from about 1:2 to about 1:6.

Aspect 33. The process defined in any one of the preceding aspects, wherein the process comprises contacting (a) and (b) in the vapor phase with (c) the catalyst (e.g., the solid catalyst).

Aspect 34. The process defined in any one of the preceding aspects, wherein the process comprises contacting (a) and (b) with a fixed bed of (c) the catalyst.

Aspect 35. The process defined in any one of the preceding aspects, wherein the process further comprises contacting (a), (b), and (c) with (d) any suitable sulfur-containing compound (e.g., $H_2S$, $CS_2$, di-tert-butyl polysulfide, etc., or any combination thereof) at any suitable amount or an amount in any range disclosed herein, e.g., less than or equal to about 5 mol %, less than or equal to about 3 mol %, or less than about 1 mol %, based on the moles of the limiting reactant.

Aspect 36. The process defined in any one of the preceding aspects, wherein the step of contacting is conducted at any suitable WHSV or a WHSV in any range disclosed herein, e.g., from about 0.01 to about 3, or from about 0.05 to about 1.

Aspect 37. The process defined in any one of the preceding aspects, wherein the catalyst comprises any suitable catalyst or any catalyst disclosed herein, e.g., a solid hydrotreating catalyst such as a CoMo catalyst or a NiMo catalyst, γ-alumina, a zeolite, or any combination thereof.

Aspect 38. The process defined in aspect 37, wherein the catalyst comprises the catalyst supported on any suitable solid oxide or any solid oxide disclosed herein, e.g., silica, alumina, silica-alumina, aluminum phosphate, zinc aluminate, zirconia, thoria, etc., or any combination thereof.

Aspect 39. The process defined in any one of the preceding aspects, wherein the conversion of the limiting reactant (or the yield to the sulfide compound having formula (II), or the yield to the ether compound having formula (I), or the yield to the ether or sulfide compound having formula (III)) is any percent conversion (or yield) disclosed herein, e.g., at least about 50%, at least about 60%, at least about 70%, at least about 80%, or at least about 90%.

Aspect 40. The process defined in any one of the preceding aspects, wherein the single pass conversion of the limiting reactant (or the single pass yield to the sulfide compound having formula (II), or the single pass yield to the ether compound having formula (I), or the single pass yield to the ether or sulfide compound having formula (III)) is any single pass percent conversion (or single pass yield) disclosed herein, e.g., at least about 40%, at least about 50%, at least about 60%, at least about 70%, or at least about 80%.

Aspect 41. The process defined in any one of the preceding aspects, wherein the reaction mixture contains less than or equal to about 5 wt. % of mercaptan reaction products, less than or equal to about 3 wt. % of mercaptan reaction products, or less than or equal to about 1 wt. % of mercaptan reaction products.

Aspect 42. The process defined in any one of the preceding aspects, further comprising a step of isolating the sulfide compound having formula (II) (or the ether compound having formula (I), or the ether or sulfide compound having formula (III)) from the reaction mixture using any suitable technique or any technique disclosed herein, e.g., extraction, filtration, evaporation, distillation, or any combination thereof, to form a product stream containing the sulfide compound having formula (II) (or the ether compound having formula (I), or the ether or sulfide compound having formula (III)).

Aspect 43. The process defined in aspect 42, wherein isolating comprises a distillation step.

Aspect 44. The process defined in aspect 42 or 43, wherein the yield of the sulfide compound having formula (II) (or the yield of the ether compound having formula (I), or the yield of the ether or sulfide compound having formula (III)) in the product stream is at least about 50%, at least about 60%, at least about 70%, or at least about 80%, based on the limiting reactant.

Aspect 45. The process defined in any one of aspects 42-44, wherein the purity of the sulfide compound having formula (II) (or the ether compound having formula (I), or the ether or sulfide compound having formula (III)) in the product stream is at least about 80 wt. %, at least about 85 wt. %, at least about 90 wt. %, at least about 95 wt. %, or at least about 98 wt. %, based on the total weight of the product stream.

Aspect 46. The process defined in any one of the preceding aspects, wherein the limiting reactant is recycled to extinction.

We claim:

1. A process for producing an ether or sulfide compound having formula (III):

$R^1$—X—$R^2$         (III);

the process comprising contacting:
(a) a first ether or sulfide compound having formula (F),

$R^1$—X—$R^1$         (F);

(b) a second ether or sulfide compound having formula (G),

$R^2$—X—$R^2$         (G); and (c) a catalyst;
to form a reaction mixture comprising the ether or sulfide compound having formula (III);
wherein:
each X independently is sulfur or oxygen;
$R^1$ is a $C_1$ to $C_{18}$ substituted or unsubstituted, cycloalkyl group or linear or branched alkyl group; and R² is a C₁ to C₁₈ substituted or unsubstituted, cycloalkyl group or linear or branched alkyl group.

2. The process of claim 1, wherein each X is sulfur.

3. The process of claim 2, wherein the sulfide compound having formula (III) is methyl ethyl sulfide, methyl iso-propyl sulfide, methyl dodecyl sulfide, ethyl octyl sulfide, or n-pentyl n-heptyl sulfide.

4. The process of claim 1, wherein each X is oxygen.

5. The process of claim 4, wherein the ether compound having formula (III) is methyl ethyl ether, methyl iso-propyl ether, methyl tert-butyl ether, or methyl tert-amyl ether.

6. The process of claim 1, wherein:
R¹ and R² independently are a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; and
R¹ and R² are different.

7. The process of claim 1, wherein the step of contacting is conducted at:
a temperature in a range from about 200° C. to about 500° C.;
a pressure in a range from about 50 to about 850 psig (344 to 5860 kPag); and
a WHSV in a range from about 0.01 to about 3.

8. The process of claim 1, wherein the compound having formula (F) and the compound having formula (G) are combined prior to contacting a fixed bed of the catalyst.

9. The process of claim 1, wherein a molar ratio of the compound having formula (F) to the compound having formula (G) is in a range from about 10:1 to about 1:10.

10. The process of claim 1, wherein the process further comprises contacting the compound having formula (F), the compound having formula (G), the catalyst, with a sulfur-containing compound comprising H₂S, CS₂, di-tert-butyl polysulfide, or any combination thereof.

11. The process of claim 1, wherein:
the reaction mixture contains less than or equal to about 5 wt. % of mercaptan reaction products;
the compound having formula (F) is a limiting reactant;
a conversion of the limiting reactant is at least about 60%; and
a yield of the compound having formula (III) is at least about 50 mol %, based on the limiting reactant.

12. The process of claim 1, wherein the catalyst comprises a supported CoMo catalyst, a supported NiMo catalyst, γ-alumina, a zeolite, or any combination thereof.

13. The process of claim 1, further comprising a step of isolating the compound having formula (III) from the reaction mixture to form a product stream containing the compound having formula (III).

14. The process of claim 13, wherein:
the compound having formula (F) is a limiting reactant;
a yield of the compound having formula (III) in the product stream is at least about 50 mol %, based on the limiting reactant; and
a purity of the compound having formula (III) in the product stream is at least about 85 wt. %, based on the total weight of the product stream.

* * * * *